United States Patent [19]

Wei

[11] Patent Number: 4,520,196

[45] Date of Patent: May 28, 1985

[54] α-MERCAPTOPHENYLACETIC ACID DERIVATIVES OF IMIDAZOLE-CONTAINING COMPOUNDS AND ANALOGUES THEREOF

[75] Inventor: Peter H. L. Wei, Springfield, Pa.

[73] Assignee: American Home Products Corporation, New York, N.Y.

[21] Appl. No.: 524,479

[22] Filed: Aug. 18, 1983

[51] Int. Cl.³ .................. C07D 239/95; C07D 235/28
[52] U.S. Cl. .................... 544/285; 544/251; 544/265; 546/82; 546/84; 548/329
[58] Field of Search .................... 548/329; 544/285

[56] References Cited

U.S. PATENT DOCUMENTS 3,558,775   1/1971   Fournier ........................ 424/232
4,214,089   7/1980   Fenichel et al. ............... 548/329 X

OTHER PUBLICATIONS

*Chemical Abstracts,* 96:85460e, (1982), [Baudy–Floch, M., et al., *Synthesis* 1981, (12), 981–983].
Duffin, G., et al., *Journal of the Chemical Society,* 1956, 361–368.
Rebstock, T., et al., *Journal of the American Chemical Society,* 78, 5831–5832, (1956).
Van Allen, J., *Journal of Organic Chemistry,* 21, 24–27, (1956).
*Chemical Abstracts,* 51, 9814i, (1957), [Rebstock, T., et al., *Plant Physiol.* 32, 19–22, (1957)].

*Primary Examiner*—Richard A. Schwartz
*Attorney, Agent, or Firm*—George Tarnowski

[57] ABSTRACT

α-Mercaptobenzylacetic acid derivatives of imidazole-containing compounds and analogues thereof, and their use as immunomodulating agents are disclosed.

9 Claims, No Drawings

α-MERCAPTOPHENYLACETIC ACID DERIVATIVES OF IMIDAZOLE-CONTAINING COMPOUNDS AND ANALOGUES THEREOF

BRIEF DESCRIPTION OF THE INVENTION

The invention relates to α-mercaptophenylacetic acid derivatives of imidazole-containing compounds and their use as immunomodulating agents.

Immunodeficiency has been considered as an important factor in oncogenesis, autoimmune disease, genetic disposition to infections, and so forth. Chemical agents capable of stimulating the cellular and/or humoral responses have been employed in the therapeutical treatment of such disorders. Immunomodulators which exert an immunostimulatory effect on the immune response can assist in the therapeutic stimulation of cellular immunity, and so are useful in the treatment of diseases involving chronic infection in vivo, such as fungal or mycoplasma infections, tuberculosis, leprosy, acute and chronic viral infections and the like. By stimulating T cell production, such compounds can be used to overcome T cell/B cell imbalance and so be useful in the therapeutic treatment of certain autoimmune diseases in which damaging antibodies are present, for example, systemic lupus erythematosus and rheumatoid arthritis.

DETAILED DESCRIPTION OF THE INVENTION

The invention is directed to novel compounds having the general formula:

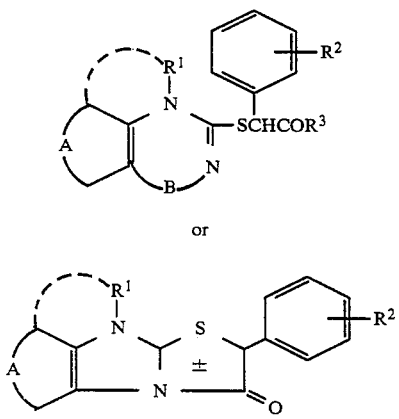

(I)

or (II)

wherein

A is a moiety having the formula

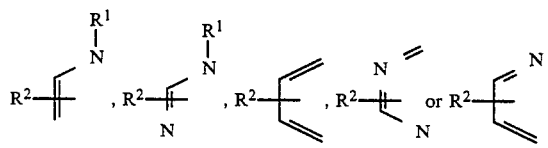

B represents a single bond or when A is

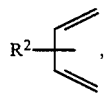

then B is the moiety

$R^1$ is hydrogen, lower alkyl or phenyl, or $R^1$ forms a saturated 5- or 6-membered heterocycle as represented by the dotted lines;

$R^2$ is hydrogen, halo, nitro, amino, lower alkylamino, lower alkyl, trifluoromethyl or lower alkanoylamino;

$R^3$ is hydroxy, lower alkoxy, amino, lower alkylamino, lower alkanoylamino, amino(lower)alkylamino, or hydroxy(lower)alkylamino;

or a pharmaceutically acceptable salt thereof.

The term "halo" is meant to encompass fluoro, chloro, and bromo. The term "lower alkyl" refers to alkyl groups being 1-4 carbon atoms. In like manner, "lower alkoxy" and "lower alkanoyl" refer to groups in which the alkyl moiety has 1-4 and 2-3 carbon atoms, respectively.

The α-mercaptophenylacetic acids of the invention can be prepared according to the following reaction sequence:

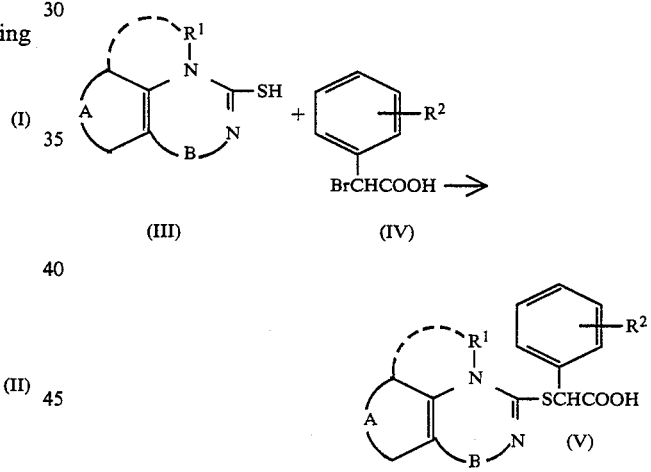

wherein $R^1$, $R^2$, A and B are as defined hereinbefore. The reaction is carried out in an organic solvent, such as, for example, acetone or methylene chloride and can be performed at room temperature or at elevated temperatures. The mercaptan intermediates (III) can be reacted in their alkali metal or alkaline earth metal salt form. The reaction can also be carried out in the presence of a scavenging agent for the liberated hydrohalide, such as a tertiary amine, for example, triethylamine.

The mercaptan intermediates in the above-outlined reaction sequence can be prepared as follows:

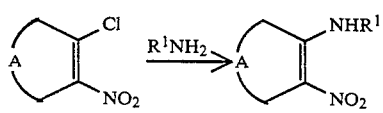

-continued

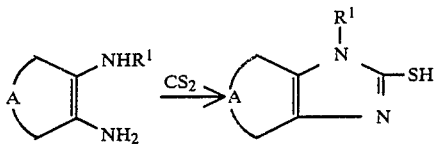

wherein R¹ and A are defined as hereinbefore. In this sequence, an appropriately substituted 2,3-diamino compound is reacted with carbon disulfide under alkaline conditions to obtain the desired mercaptan intermediates. In the case of compounds of formula I in which B is the moiety

or where R¹ forms a saturated 5- or 6-membered heterocycle as indicated by the dotted lines in formula I, the mercaptan intermediates are either commercially available or can be prepared by conventional methods. Thus, a compound such as 2-mercapto-4(3H)-quinazolinone is commercially available, while compounds such as 2-mercapto-[5,6-dihydro-4H-imidazo[4,5-ij]quinoline] can be prepared in the same manner as the mercaptan intermediates discussed supra, e.g.:

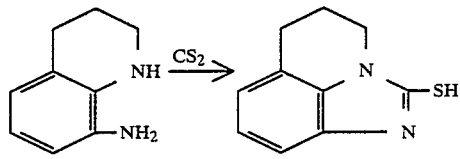

where the starting 8-amino-1,2,3,4-tetrahydroquinoline is available commercially.

The acids of formula V can also be transformed into their mesoionic didehydro derivatives:

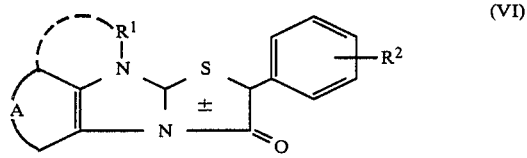

(VI)

wherein R¹, R² and A are as defined hereinbefore. The transformation can be carried out by dissolving the acids of formula V in methylene chloride and then cyclizing in the presence of acetic anhydride at reflux (separating the organic and aqueous layers), and concentrating the organic (methylene chloride) layer to recover the mesoionic didehydro derivative, which can then be further purified by recrystallization.

The acid derivatives of the acids of formula V where R³ is other than hydroxy are conveniently prepared by reacting the tricyclic mesoionic didehydro compounds described supra with appropriate nucleophilic reactants. This reaction, involving the ring cleavage of the terminal thiazole ring, is as follows:

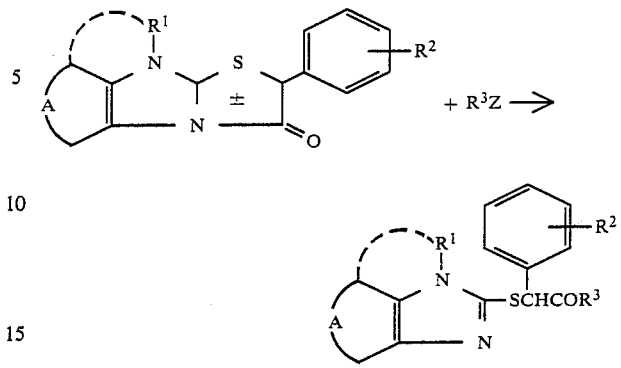

wherein R¹, R², R³, and A are as described hereinbefore and R³Z is a nucleophilic reactant bearing the desired R³ substituent. This reaction provides compounds of the invention which are otherwise inaccessible by conventional means. The reaction is carried out in a suitable organic solvent, such as, for example, methylene chloride, and over a range of temperatures, such as, room temperature, as well as under reflux conditions, depending on the nature of the nucleophilic reactant being used.

The compounds of the invention are active immunomodulators, having a stimulatory effect on the immune response. The compounds have therapeutic application in a variety of situations in which immunomodulation is indicated. Thus, the compounds are useful in the treatment of diseases involving chronic infections, in the treatment of autoimmune diseases, such as, systemic lupus erythematosus, and some diseases in which a condition of immune deficiency exists, such as, Hodgkins disease. Further, the compounds of the invention are also of use in the treatment of conditions such as rheumatoid arthritis.

When the compounds of the invention are employed as immunomodulators, they can be formulated into oral dosage forms such as tablets, capsules and the like. The compounds can be administered alone or by combining them with conventional carriers, such as, magnesium carbonate, magnesium stearate, talc, sugar, lactose, pectin, dextrin, starch, gelatin, tragacanth methyl cellulose, sodium carboxymethyl cellulose, low melting wax, cocoa butter, and the like. Diluents, flavoring agents, solubilizers, lubricants, suspending agents, binders, tablet-disintegrating agents and the like may be employed. The compounds may be encapsulated with or without other carriers. In all cases the proportion of active ingredients in said compositions both solid and liquid will be at least sufficient to impart immunomodulatory activity thereto on oral administration. The compounds may also be injected parenterally, in which case they are used in the form of a sterile solution containing other solutes, for example, enough saline or glucose to make the solution isotonic.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration level that will generally afford effective results without causing any harmful or deleterious side effects.

The following examples show the preparation and pharmacological testing of compounds embraced by the invention.

EXAMPLE 1

α-[(1-Methyl-1H-benzimidazol-2-yl)thio]benzeneacetic acid

An acetone solution of 6.5 g (0.032M) of the potassium salt of 2-mercapto-1-methyl-benzimidazole and 9.7 g (0.045M) of α-bromophenylacetic acid is stirred at room temperature overnight. The solid which is collected is washed with water and the filtrate is concentrated to remove the solvent. The combined materials are recrystallized from acetonitrile. The recrystallized material weighs 8.3 g (87% yield) and melts at 157°–9° C.

Analysis for: $C_{16}H_{14}N_2O_2S$: Calculated: C, 64.41; H, 4.73; N, 9.39. Found: C, 64.57; H, 4.92; N, 9.41.

EXAMPLE 2

4-Chloro-α-[(1-methyl-1H-benzimidazol-2-yl)thio]-benzeneacetic acid

A methylene chloride solution of 3.3 g (0.02M) of 2-mercapto-1-methyl-1H-benzimidazole, 5.0 g (0.02M) of α-bromo-(p-chlorophenyl)acetic acid and 4.0 g (0.04M) of triethylamine is heated to reflux overnight. The reaction mixture is neutralized with a diluted HCL solution. The layers are separated and the organic layer is dried over anhydrous magnesium sulfate. After removal of methylene chloride the residue is recrystallized from acetonitrile. The recrystallized material weighs 4.1 g (41% yield) and has a melting point of 161°–3° C. dec.

Analysis for: $C_{16}H_{13}ClN_2O_2S$: Calculated: C, 57.75; H, 3.94; N, 8.42. Found: C, 57.68; H, 3.96; N, 8.48.

EXAMPLE 3

α-[(5(or 6)-Chloro-1H-benzimidazol-2-ylz)-thio]benzeneacetic acid

A methylene chloride solution of 4.4 g (0.03M) of 5-chloro-2-mercaptobenzimidazole, 6.5 g (0.03M) of α-bromophenylacetic acid and 6.0 g (0.06M) of triethyleneamine is heated to reflux overnight. The reaction mixture is neutralized with a dilute HCl solution. The resultant gummy solid is triturated with water and then recrystallized from acetonitrile. The recrystallized material weighs 5.5 g (58% yield) and melts at 189°–91° C. dec.

Analysis for: $C_{15}H_{11}ClN_2O_2S \cdot \frac{1}{2}H_2O$: Calculated: C, 54.96; H, 3.69; N, 8.55. Found: C, 55.40; H, 3.54; N, 8.68.

EXAMPLE 4

α-[(7H-(or 9H)-purin-8-yl)thio]benzeneacetic acid hydrate

A methylene chloride solution of 4.6 g (0.03M) of 8-mercapto-7H-(or 9H)purine, 6.5 g (0.03M) of α-bromophenylacetic acid and 6.0 g (0.06M) of triethylamine is heated overnight. Solvent is removed and the residue dissolved in water. Upon neutralization, a gummy solid separates out which upon trituration with hot acetonitrile is collected. The crude material is recrystallized from a mixture of acetonitrile and water. The recrystallized material weighs 3.0 g (35% yield) and melts at 148°–50° C.

Analysis for: $C_{13}H_{10}N_4O_2S \cdot H_2O$: Calculated: C, 51.30; H, 3.94; N, 18.41. Found: C, 51.36; H, 4.04; N, 18.38.

EXAMPLE 5

α-[(5,6-dihydro-4H-imidazo[4,5-ij]quinolin-2-yl)thio]-benzeneacetic acid

A. 2-Mercapto-5,6-dihydro-4H-imidazo[4,5-ij]quinoline

To a solution of 26 g (0.176M) of 8-amino-1,2,3,4-tetrahydroquinoline in 200 ml of 95% ethanol is added 15 g (0.20M) of carbon disulfide. The solution is heated to gentle reflux for 24 hours. The solid which precipitates upon cooling is collected and recrystallized from 400 ml ethanol. A total of 23 g (69% yield) is recovered with a melting point of 208°–9° C.

B. α-[(5,6-dihydro-4H-imidazo[4,5-ij]quinolin-2-yl)thio]benzeneacetic acid

An acetone solution of 2-mercapto-[(5,6-dihydro-4H-imidazo[4,5-ij]quinoline] (7.2 g or 0.041M) and 9.2 g (0.042M) of α-bromophenylacetic acid (9.0 g or 0.042M) containing 40 ml each of glacial acetic acid and acetic anhydride is heated to gentle reflux overnight. The HBr salt is collected and then disproportionated by stirring in water for 5 hours. The collected solid upon recrystallization from dimethylformamide and acetonitrile weighs 5.3 g (40% yield) and melts at 184°–5° C. dec.

Analysis for: $C_{18}H_{16}N_2O_2S$: Calculated: C, 66.64; H, 4.97; N, 8.64. Found: C, 66.64; H, 5.08; N, 8.72.

EXAMPLE 6

α-[(1H-benzimidazol-2-yl)thio]benzeneacetic acid

An acetone solution of 13.5 g (0.09M) of 2-mercaptobenzimidazole and 19.4 g (0.09M) of α-bromophenylacetic acid containing 10 ml glacial acetic acid is heated for 3 hours. The solid HBr salt upon removal of the solvent is disproportionated by stirring in 1 L of water. The crude material is recrystallied from aqueous acetone. The recrystallized material weighs 24.0 g (92% yield) and melts at 187°–8° C. dec.

Analysis for: $C_{15}H_{12}N_2O_2S$: Calculated: C, 63.36; H, 4.25; N, 9.85. Found: C, 63.06; H, 4.19; N, 9.73.

EXAMPLE 7

α-[(5-Chloro-1-methylbenzimidazol-2-yl)thio]benzeneacetic acid

A. 4-Chloro-2-nitro-N-methylaniline

To 60.0 g (0.31M) of 2,4-dichloronitrobenzene in 200 ml of dimethylformamide, monomethylamine is introduced in a stream for a duration of 3 hours. The mixture is heated to gentle reflux overnight. The solvent is removed and the residual heavy oil is dissolved in methylene chloride. The methylene chloride is washed with water and the methylene chloride layer, to which some decoloring carbon is added, is dried over anhydrous magnesium sulfate. After filtering off the drying agent and the decoloring carbon, the methylene chloride is removed. The residual solid is recrystallized from hexane. The substituted aniline weighs 28.0 g (48% yield) and has a melting point of 105°–6° C.

Analysis for: $C_7H_7ClN_2O_2$: Calculated: C, 45.30; H, 3.26; N, 15.10. Found: C, 44.85; H, 3.73; N, 15.23.

A minor product, 4-chloro-2-nitro-N,N-dimethylaniline is also isolated, m.p. 54°-5° C.

Analysis for: $C_8H_9ClN_2O_2$: Calculated: C, 47.89; H, 4.52; N, 13.96. Found: C, 48.22; H, 4.65; N, 13.83.

B. 4-Chloro-1-methyl-o-phenylenediamine 32.5 g (0.175M) of 4-Chloro-2-nitro-N-methylaniline of A above are added gradually to 24 g Raney-Nickel (wet) and 48 g hydrazine in methanol. A large amount of heat is generated. After the addition is complete, the solution is heated to reflux for 3 hours and filtered to remove the metal catalyst. The solvent is removed and the residue dissolved in methylene chloride. The methylene chloride solution is extracted with water and the mixture is filtered to remove the emulsion. The layers are separated and the methylene chloride layer is dried over anhydrous magnesium sulfate. After removal of the solvent, the residue is recrystallized from hexane. The substituted phenylenediamine weighs 22.6 g (84% yield) and has a melting point of 51°-2° C.

Analysis for: $C_7H_9ClN_2$: Calculated: C, 53.68; H, 5.79; N, 17.89. Found: C, 53.26; H, 5.74; N, 17.47.

C. 5-Chloro-2-mercapto-1-methylbenzimidazole 14.0 g (0.071M) of 4-Chloro-1-methyl-o-phenylenediamine of B above, 7.2 g (0.129M) of potassium hydroxide and 8.7 g (0.114M) of carbon disulfide are heated to reflux in 200 ml water for 5 hours. A solid is collected, and by neutralization of the filtrate, more is recovered. The crude materials are recrystallized from acetonitrile to give 15 g, which represents 88% yield of mercaptan, m.p. 232°-4° C.

Analysis for: $C_8H_7ClN_2S$: Calculated: C, 48.36; H, 3.55; N, 14.10. Found: C, 48.60; H, 3.67; N, 14.19.

D. α-[(5-Chloro-1-methylbenzimidazol-2-yl)thio]benzeneacetic acid 5.96 g (0.03M) of 5-Chloro-2-mercapto-1-methylbenzimidazole of C above, 0.5 g (0.03M) of α-bromophenylacetic acid and 6.0 g (0.06M) of triethylamine are dissolved in methylene chloride (200 ml) and the mixture heated to reflux overnight. The basic solution is washed with a diluted HCl solution and a white solid is collected. The crude material is recrystallized from 5 L of acetonitrile to give 6.0 g (60% yield) of the title compound, m.p. 203°-5° C. dec.

Analysis for: $C_{16}H_{13}ClN_2O_2S$: Calculated: C, 57.74; H, 3.94; N, 8.42. Found: C, 57.57; H, 4.10; N, 8.47.

EXAMPLE 8

α-[(3,4-Dihydro-4-oxo-2-quinazolinyl)thio]benzeneacetic acid

A methylene chloride solution of 8.9 g (0.05M) of 2-mercapto-4(3H)-quinazolinone, α-bromophenylacetic acid and triethylamine is heated to gentle reflux for 48 hours. A small amount of insoluble material is filtered off and then the solvent is removed. The oily residue is dissolved in water and insoluble material filtered off. The aqueous filtrate is acidified with a dilute HCl solution and the gummy solid is extracted with methylene chloride. The methylene chloride solution is dried over anhydrous magnesium sulfate. After the solvent is removed the residual solid is dissolved in 500 ml hot acetonitrile, and upon cooling the solid is filtered. The filtrate, upon standing, gives 5.0 g (31% yield) of product which has a melting point of 184°-5° C. dec.

Analysis for: $C_{16}H_{12}N_2O_3S \cdot H_2O$: Calculated: C, 58.17; H, 4.27; N, 8.48. Found: C, 58.10; H, 4.39; N, 8.66.

EXAMPLE 9

α-[(3-Methylimidazo[5,4-b]pyridin-2-yl)thio]benzeneacetic acid

A. 2-Methylamino-3-nitropyridine 25 g (0.16M) of 2-chloro-3-nitropyridine is dissolved in 200 ml dimethylformamide. For three hours monomethylamine is bubbled into the solution. The mixture is heated to reflux overnight. After the solvent is removed the oily residue is triturated with water and the solid is collected and air dried. The crude material is recrystallized from hexane to give 19.5 g (80% yield) of title compound, melting point 62°-3° C.

Analysis for: $C_6H_7N_3O_2$: Calculated: C, 47.05; H, 4.61; N, 27.44. Found: C, 46.92; H, 4.73; N, 27.13.

B. 2-N-methyl-2,3-diaminopyridine

The nitro compound of A above is reduced catalytically in the presence of 10% palladium on charcoal in ethanol. The residue, after removal of solvent, is recrystallized in either benzene or cyclohexane to give 86% yield, melting point 98°-9° C.

Analysis for: $C_6H_9N_3$: Calculated: C, 58.51; H, 7.37; N, 34.12. Found: C, 58.29; H, 7.26; N, 33.66.

C. 2-Mercapto-3-methylimidazo[5,4-b]pyridine

To 17.5 g (0.142M) of the amine in B above in 400 ml water is added 14.5 g (0.258M) potassium hydroxide followed by 17.3 g (0.228M) carbon disulfide. The mixture is heated to gentle reflux for 4 hours. After the solid is filtered off the filtrate is acidified with acetic acid and the solid is also collected. The combined solids are recrystallized from acetonitrile to give 20 g of mercaptan, which represents 87% yield, melting point 265° C. dec.

Analysis for: $C_7H_7N_3S$: Calculated: C, 50.88; H, 4.27; N, 25.44. Found: C, 51.04; H, 4.33; N, 25.51.

D. α-[(3-Methylimidazo[5,4-b]pyridin-2-yl)thio]benzeneacetic acid

A methylene chloride solution of 6.6 g (0.04M) of the mercaptan of C above, 8.6 g (0.04M) α-bromophenylacetic acid and 8.0 g (0.08M) triethylamine is heated to reflux overnight. After the reaction mixture is washed with a diluted HCl solution, the solution is dried over anhydrous magnesium sulfate. Upon removal of the drying agent, the methylene chloride is removed and the residual solid is recrystallized from benzene. The recrystallized material weighs 9.0 g (75% yield) and melts at 83°-5° C. dec.

Analysis for: $C_{15}H_{13}N_3O_2S$: Calculated: C, 60.18; H, 4.38; N, 14.04. Found: C, 60.15; H, 4.59; N, 13.84.

EXAMPLE 10

α-[(1-Phenylbenzimidazol-2-yl)thio]benzeneacetic acid

A. 2-Mercapto-1-phenylbenzimidazole

To 18.6 g (0.10M) of N-phenyl-o-phenylenediamine in 100 ml ethanol, 4.8 g (0.12M) of sodium hydroxide in 20 ml water is added followed by 13 g (0.17M) of carbon disulfide. The mixture is heated to reflux for 5 hours. The reaction mixture is poured into 300 ml water and solid is collected. The crude material is recrystallized from ethanol and the recrystallized material weighs 25 g (74% yield) and melts at 195°-7° C.

Analysis for: $C_{13}H_{10}N_2S$: Calculated: C, 68.99; H, 4.45; N, 12.38. Found: C, 68.91; H, 4.24; N, 12.60.

B. α-[(1-Phenylbenzimidazol-2-yl)thio]benzeneacetic acid

A methylene chloride solution of 6.7 g (0.03M) of the mercaptan in A above, 6.4 g (0.03M) α-bromophenylacetic acid and 6.0 g triethylamine is heated to reflux for 20 hours. The reaction mixture is washed with a diluted HCl solution. The methylene chloride solution is dried over anhydrous magnesium sulfate. After the drying agent is removed, the filtrate is evaporated to remove the methylene chloride and the residue is recrystallized from acetonitrile. The recrystallized material weighs 8.0 g (74% yield) and melts at 179°–80° C. dec.

Analysis for: $C_{21}H_{16}N_2O_2S$: Calculated: C, 69.98; H, 4.47; N, 7.77. Found: C, 69.99; H, 4.62; N, 7.54.

EXAMPLE 11

2,9-diphenyl-9H-thiazolo[3,2-a]benzimidazol-3(2H)-one didehydro mesoionic derivative a solution of 4.3 g (0.012M) of α-[(1-phenyl-1H-benzimidazol-2-yl)thio]benzeneacetic acid, prepared according to Example 10, in 100 ml methylene chloride and 10 ml acetic anhydride is heated to gentle reflux overnight. After the solvent is removed, the residual solid upon trituration with ether is collected and recrystallized from acetonitrile. The title compound weighs 2.1 g (51% yield) and melts at 202°–4° C.

Analysis for: $C_{21}H_{14}N_2OS$: Calculated: C, 73.66; H, 4.12; H, 8.18. Found: C, 73.32; H, 4.19; N, 8.30.

EXAMPLE 12

6-Chloro-9-methyl-2-phenyl-9H-thiazolo[3,2-a]benzimidazol-3-(2H)-one didehydro mesoionic derivative Following the same procedure as in Example 11, and substituting α-[(5-chloro-1-methyl-1H-benzimidazol-2-yl)thio]benzeneacetic acid, prepared according to Example 7, for α-[(1-phenyl-1H-benzimidazol-2-yl)thio]benzeneacetic acid, the title compound is prepared in 76% yield with a melting point of 213°–4° C.

Analysis for: $C_{16}H_{13}ClN_2OS$: Calculated: C, 61.04; H, 3.52; N, 8.90. Found: C, 60.78; H, 3.79; N, 8.67.

EXAMPLE 13

9-Methyl-2-phenyl-9H-thiazolo[3,2-a]benzimidazol-3(2H)-one didehydro mesoionic derivative Following the procedure of Example 11 and substituting α-[(1-methyl-1H-benzimidazol-2-yl)thio]benzeneacetic acid, prepared according to Example 1, for α-[(1-phenyl-1H-benzimidazol-2-yl)thio]benzeneacetic acid, the title compound is prepared in 82% yield with a decomposition point at 180° C.

Analysis for: $C_{16}H_{12}N_2OS$: Calculated: C, 68.55; H, 4.31; N, 9.99. Found: C, 68.19; H, 4.55; N, 9.97.

EXAMPLE 14

9-Methyl-2-phenyl-9H-thiazolo[3',2':1,2]imidazol[4,5-b]pyridin-3(2H)-one didehydro mesoionic derivative Following the procedure of Example 11 and substituting α-[(3-methylimidazo[5,4-b]pyridin-2-yl)thio]benzeneacetic acid, prepared according to Example 9, for α-[(1-phenyl-1H-benzimidazol-2-yl)thio]benzeneacetic acid, the title compound is prepared in 68% yield with a melting point of 185°–6° C.

Analysis for: $C_{15}H_{11}N_3OS$: Calculated: C, 64.04; H, 3.94; N, 14.94. Found: C, 64.15; H, 4.13; N, 14.99.

EXAMPLE 15

9,10-Dihydro-2-phenyl-8H-thiazolo[2',3':2,3]imidazo[4,5,1]-[i,j]quinolin-3-(2H)-one mesoionic didehydro derivative Following the procedure of Example 11 and substituting α-[(5,6-dihydro-4H-imidazo[4,5-i,j]quinolin-2-yl)thio]benzeneacetic acid, prepared according to Example 5, for α-[(1-phenyl-1H-benzimidazol-2-yl)thio]benzeneacetic acid, the title compound is prepared in 33% yield with a decomposition point of 170°–1° C.

Analysis for: $C_{18}H_{14}N_2OS \cdot H_2O$: Calculated: C, 66.64; H, 4.97; N, 8.64. Found: C, 66.53; H, 4.94; N, 8.40.

EXAMPLE 16

α-[(1-Methyl-1H-benzimidazol-2-yl)thio]benzeneacetic acid ethyl ester 1.0 g (0.004M) of 9-methyl-2-phenyl-9H-thiazolo[3,2-a]-benzimidazol-3(2H)-one didehydro mesoionic derivate, prepared according to Example 13, is suspended in 20 ml absolute ethanol and the mixture is heated on a steam bath. The completion of the reaction is indicated by the discoloration of the reaction mixture. After the solvent is removed, the residual solid is recrystallized from ether. The title compound weighs 0.8 g (62% yield) and melts at 103°–4° C.

Analysis for: $C_{18}H_{18}N_2O_2S$: Calculated: C, 66.23; H, 5.56; N, 8.58. Found: C, 66.02; H, 5.61; N, 8.46.

EXAMPLE 17

α-[(1-Methyl-1H-benzimidazol-2-yl)thio]benzeneacetamide

To a methylene chloride solution of 3.4 g (0.0137M) of 9-methyl-2-phenyl-9H-thiazolo[3,2-a]benzimidazol-3(2H)-one didehydro mexoionic derivative, prepared according to Example 13, ammonia is introduced until the discoloration of the reaction mixture is complete. The collected solid is recrystallized from 50 ml of acetonitrile. The title compound weighs 2.5 g (61% yield) and melts at 185°–7° C.

Analysis for: $C_{16}H_{15}N_3OS$: Calculated: C, 64.62; H, 5.08; N, 14.13. Found: C, 64.48; H, 5.09; N, 13.88.

EXAMPLE 18

The activity of the compounds is determined according to the following procedure:

T lymphocytes are isolated from spleens of 3 month old male CBA/J mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% $CO_2$, for 45 minutes. The nonadherant T lymphocytes are then eluted from the column, counted, and adjusted to $20 \times 10^6$ cells/ml 50 μl of cells are cultured (37° C., 95% air, 5% $CO_2$) with a suboptimal concentration of Concanavalin A plus compound, for 48 hours before addition of 0.5 μCi. of 3H-thymidine for the last 16 hours of culture. The total volume of the culture system in 200 μl. The cells are then harvested on a multiple automatic sample harvester (Mash II), the glass fiber filter disks placed in 10 ml of xylene base scintillation fluid, and counted for 1 minute in a liquid scintillation counter. Results are reported as CPM±SE. Comparisons are made between counts obtained with control cultures and cultures containing compound and a determination made as to whether the compounds are active at the dosage tested.

The results are summarized below:

| Compound or Example No. | | Concentration (μg/culture) | 3H—Thymidine Uptake CPM + S.E. |
|---|---|---|---|
| A. | Concanavalin A | 0.025 | 4,733 ± 343 |
| | Concanavalin A + | 0.0025 | 5,910 ± 189 |
| | Example 1 | 0.01 | 5,671 ± 241 |
| | | 0.05 | 5,482 ± 266 |
| | | 0.1 | 6,029 ± 361 |
| | | 1.0 | 8,979 ± 391 |
| | | 2.0 | 10,945 ± 320 |
| | | 3.0 | 12,388 ± 337 |
| | | 5.0 | 11,970 ± 337 |
| (A) | Concanavalin A | 0.04 | 42,374 ± 1,283 |
| | Concanavalin A + | 0.0025 | 43,911 ± 1,242 |
| | Example 1 | 0.01 | 46,225 ± 892 |
| | | 0.1 | 43,863 ± 554 |
| | | 1.0 | 44,386 ± 1,366 |
| | | 5.0 | 36,705 ± 828 |
| | | 10.0 | 28,295 ± 535 |
| B. | Concanavalin A | 0.05 | 85,027 ± 6,676 |
| | Concanavalin A + | 0.01 | 109,133 ± 3,986 |
| | Example 5 | 0.1 | 113,643 ± 2,766 |
| | | 1.0 | 99,096 ± 3,270 |
| | | 2.0 | 68,625 ± 3,086 |
| | | 5.0 | 18,625 ± 928 |
| C. | Concanavalin A | 0.025 | 30,346 ± 693 |
| | Concanavalin A + | 0.0025 | 36,520 ± 990 |
| | Example 10 | 0.01 | 35,340 ± 854 |
| | | 0.1 | 33,641 ± 1,033 |
| | | 1.0 | 33,377 ± 968 |
| | | 5.0 | 3,871 ± 96 |
| | | 10.0 | 217 ± 15 |
| D. | Concanavalin A | 0.04 | 12,150 ± 735 |
| | Concanavalin A + | 0.01 | 14,543 ± 397 |
| | Example 2 | 0.1 | 13,015 ± 324 |
| | | 1.0 | 12,905 ± 718 |
| | | 2.0 | 12,106 ± 216 |
| | | 5.0 | 8,777 ± 678 |
| E. | Concanavalin A | 0.04 | 42,374 ± 1,283 |
| | Concanavalin A + | 0.0025 | 44,721 ± 3,320 |
| | Example 7 | 0.01 | 46,085 ± 589 |
| | | 0.1 | 46,362 ± 695 |
| | | 1.0 | 46,339 ± 2,051 |
| | | 5.0 | 26,459 ± 978 |
| | | 10.0 | 12,700 ± 870 |
| F. | Concanavalin A | 0.05 | 41,832 ± 2,448 |
| | Concanavalin A + | 0.01 | 66,300 ± 3,506 |
| | Example 3 | 0.1 | 64,663 ± 6,077 |
| | | 1.0 | 68,094 ± 3,280 |
| | | 5.0 | 65,074 ± 6,422 |

The results show that at low dosage levels the compounds tested increased lymphocyte proliferation of T cells stimulated by the mitogen, Concanavalin A, evidencing a strong stimulator activity.

What is claimed is:

1. A compound having the formula:

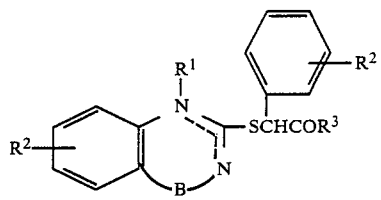

wherein

B represents a single bond or the moiety

$R^1$ is hydrogen, lower alkyl or phenyl;

$R^2$ is hydrogen, halo, nitro, amino, lower alkylamino, lower alkyl, trifluoromethyl or lower alkanoylamino;

$R^3$ is hydroxy, lower alkoxy, amino, lower alkylamino, lower alkanoylamino, amino(lower)alkylamino, or hydroxy(lower)alkylamino; the dotted lines represent either a single or a double bond; with the proviso that when $R^1$ is hydrogen, the $R^2$ substituent on the benzofused moiety is other than hydrogen;

or a pharmaceutically acceptable salt thereof.

2. The compound of claim 1 having the name α-[(1-methyl-1H-benzimidazol-2-yl)thio]benzeneacetic acid.

3. The compound of claim 1 having the name 4-chloro-α-[(1-methyl-1H-benzimidazol-2-yl)thio]benzeneacetic acid.

4. The compound of claim 1 having the name α-[(5 (or 6)-chloro-1H-benzimidazol-2-yl)thio]benzeneacetic acid.

5. The compound of claim 1 having the name α-[(5-chloro-1-methylbenzimidazol-2-yl)thio]benzeneacetic acid.

6. The compound of claim 1 having the name α-[(3,4-dihydro-4-oxo-2-quinazolinyl)thio]benzeneacetic acid.

7. The compound of claim 1 having the name α-[(1-phenylbenzimidazol-2-yl)thio]benzeneacetic acid.

8. The compound of claim 1 having the name α-[(1-methyl-1H-benzimidazol-2-yl)thio]benzeneacetic acid ethyl ester.

9. The compound of claim 1 having the name α-[(1-methyl-1H-benzimidazol-2-yl)thio]benzeneacetamide.

* * * * *